US009604046B2

(12) United States Patent
Steele

(10) Patent No.: US 9,604,046 B2
(45) Date of Patent: Mar. 28, 2017

(54) PROTECTIVE CAPS FOR USE WITH MEDICAL FLUID FITTINGS, AND RELATED METHODS

(71) Applicant: Nordson Corporation, Westlake, OH (US)

(72) Inventor: Kyle R. Steele, Windsor, CO (US)

(73) Assignee: NORDSON CORPORATION, Westlake, OH (US)

(*) Notice: Subject to any disclaimer, the term of this patent is extended or adjusted under 35 U.S.C. 154(b) by 95 days.

(21) Appl. No.: 14/530,939

(22) Filed: Nov. 3, 2014

(65) Prior Publication Data
US 2016/0121097 A1 May 5, 2016

(51) Int. Cl.
*A61M 39/20* (2006.01)
*F16L 35/00* (2006.01)
*F16L 55/115* (2006.01)
*A61M 39/16* (2006.01)
*A61M 39/10* (2006.01)
*A61M 5/31* (2006.01)

(52) U.S. Cl.
CPC .......... *A61M 39/20* (2013.01); *F16L 35/00* (2013.01); *F16L 55/1152* (2013.01); *A61M 39/165* (2013.01); *A61M 2005/3104* (2013.01); *A61M 2039/1083* (2013.01)

(58) Field of Classification Search
USPC ................ 215/228, 356; 285/92, 332, 334.4
See application file for complete search history.

(56) References Cited

U.S. PATENT DOCUMENTS 3,307,552 A * 3/1967 Strawn .................. A61M 39/20
   138/89
4,340,148 A * 7/1982 Beckham ............ A61M 1/3627
   215/247

(Continued)

FOREIGN PATENT DOCUMENTS

WO          0024442 A1      5/2000
WO       2011066586 A1      6/2011

OTHER PUBLICATIONS

Value Plastics, Inc., A Nordson Company, Luer Fittings, Catalog Pages., Dec. 2013.

(Continued)

*Primary Examiner* — J. Gregory Pickett
*Assistant Examiner* — Gideon Weinerth
(74) *Attorney, Agent, or Firm* — Baker & Hostetler LLP

(57) ABSTRACT

A protective cap for use with a medical fluid fitting including a fitting thread and a sealing portion having a sealing surface. The protective cap includes a body having a proximal end, a distal end, and a cap thread extending axially. The cap thread is configured to threadedly engage the fitting thread for releasably coupling the protective cap with the medical fluid fitting, and defines a tapered engagement surface. The tapered engagement surface tapers axially relative to a longitudinal axis of the body, and is configured to frictionally contact the fitting thread for retaining the protective cap in coupling engagement with the medical fluid fitting. The protective cap is configured to peripherally surround the sealing portion such that no portion of the protective cap contacts the sealing surface when the protective cap is coupled with the medical fluid fitting.

21 Claims, 18 Drawing Sheets

(56) References Cited

U.S. PATENT DOCUMENTS

| | | | | |
|---|---|---|---|---|
| 4,991,629 | A * | 2/1991 | Ernesto | A61M 39/20 138/89 |
| 5,176,415 | A * | 1/1993 | Choksi | A61M 39/10 128/202.27 |
| 5,184,742 | A * | 2/1993 | DeCaprio | A61M 39/20 215/356 |
| 5,224,515 | A * | 7/1993 | Foster | B65D 59/06 138/89 |
| 5,290,253 | A * | 3/1994 | Kira | A61M 39/20 604/190 |
| 5,620,427 | A * | 4/1997 | Werschmidt | A61M 39/10 137/516.13 |
| 5,954,657 | A * | 9/1999 | Rados | A61M 39/20 600/486 |
| 5,984,373 | A * | 11/1999 | Fitoussi | A61M 5/3213 285/332 |
| 6,152,913 | A | 11/2000 | Feith et al. | |
| 6,261,270 | B1 * | 7/2001 | Gault | A61M 39/04 604/246 |
| 6,394,983 | B1 * | 5/2002 | Mayoral | A61M 39/20 604/192 |
| D517,209 | S * | 3/2006 | Burton | D24/129 |
| 7,316,669 | B2 * | 1/2008 | Ranalletta | A61M 5/3134 604/199 |
| 8,777,931 | B2 * | 7/2014 | Davis | A61M 39/10 285/332 |
| 2004/0133169 | A1 * | 7/2004 | Heinz | A61M 5/3134 604/187 |
| 2009/0194730 | A1 * | 8/2009 | Clawson | A61M 39/26 251/366 |
| 2010/0198138 | A1 * | 8/2010 | Chapman | A61M 1/285 604/29 |
| 2011/0165020 | A1 * | 7/2011 | Tryggvason | A61L 2/18 422/28 |
| 2011/0309615 | A1 * | 12/2011 | Arstein | F16L 19/061 285/332 |
| 2012/0302997 | A1 * | 11/2012 | Gardner | A61M 39/20 604/533 |
| 2013/0197485 | A1 * | 8/2013 | Gardner | A61M 39/162 604/533 |
| 2014/0276651 | A1 * | 9/2014 | Schultz | A61M 39/165 604/535 |

OTHER PUBLICATIONS

European Application No. 15192340: Extended European Search Report dated Jan. 21, 2016, 6 pages.

* cited by examiner

PROTECTIVE CAPS FOR USE WITH MEDICAL FLUID FITTINGS, AND RELATED METHODS

TECHNICAL FIELD

The present invention relates generally to medical fluid fittings, and more particularly, to caps for protecting sealing surfaces on medical fluid fittings.

BACKGROUND

Various types of fittings, or connectors, are often used for interconnecting conduit and other components in medical applications for conveying fluids. Such medical fluid fittings include a sealing portion having a sealing surface for forming a fluid-tight seal when mated with a corresponding sealing surface of a mating component, thereby ensuring reliable transfer of fluids. Such fittings and their corresponding sealing portions may be male or female. For example, FIG. 1A shows a cross-sectional view of a known male medical fluid fitting 1, including a male sealing portion 2 having a tapered sealing surface 3 for insertion into a mating component for forming a releasable seal with an inner surface thereof. FIG. 1B shows a cross-sectional view of a known female medical fluid fitting 4, including a female sealing portion 5 having a socket 6 and a tapered sealing surface 7 for receiving a mating component and forming a releasable seal with an outer surface thereof.

When the sealing surface of a medical fluid fitting is not in use, the sealing portion is preferably fitted with a protective cap to maintain the sealing surface free from debris and damage from warping, scratching, galling, and other malformations caused by surface contact. In this manner, the sealing surface may be preserved for optimal sealing performance. Preferably, the protective cap remains securely attached to the fitting such that the cap does not inadvertently detach from the fitting due to vibrations or impacts, such as those experienced during shipping and handling. Traditional caps rely on direct engagement with the sealing surface for maintaining a secure attachment to the fitting and retaining the cap in its protective position. However, such direct engagement may compromise the integrity of the sealing surface and thereby hinder the ability of the sealing surface to form an effective seal with a mating component during use.

Accordingly, there is a need for improved protective caps for use with medical fluid fittings that address the present challenges such as those discussed above.

SUMMARY

An exemplary embodiment of protective cap is provided for use with a medical fluid fitting that is configured to convey a fluid therethrough. The medical fluid fitting includes a fitting thread and a sealing portion having a sealing surface for forming a fluid tight seal with a mating part. The protective cap includes a body having a proximal end and a distal end, and a cap thread provided on the body and extending axially. The cap thread is configured to threadedly engage the fitting thread for releasably coupling the protective cap with the medical fluid fitting. The protective cap further includes a tapered engagement surface defined by the cap thread and tapering axially relative to a longitudinal axis of the body. The tapered engagement surface is configured to frictionally contact the fitting thread for retaining the protective cap in coupling engagement with the medical fluid fitting. The protective cap is configured to peripherally surround the sealing portion such that no portion of the protective cap contacts the sealing surface when the protective cap is coupled with the medical fluid fitting.

An exemplary medical fluid fitting assembly includes a medical fluid fitting configured to convey a fluid therethrough. The medical fluid fitting includes a fitting thread and a sealing portion having a sealing surface for forming a fluid tight seal with a mating part. The medical fluid fitting assembly further includes a protective cap configured to protect the sealing surface of the medical fluid fitting. The protective cap includes a body having a proximal end and a distal end, and a cap thread provided on the body and extending axially. The cap thread is configured to threadedly engage the fitting thread for releasably coupling the protective cap with the medical fluid fitting. The protective cap further includes a tapered engagement surface defined by the cap thread and tapering axially relative to a longitudinal axis of the body. The tapered engagement surface is configured to frictionally contact the fitting thread for retaining the protective cap in coupling engagement with the medical fluid fitting. The protective cap peripherally surrounds the sealing portion without contacting the sealing surface when the protective cap is coupled with the medical fluid fitting.

In use, an exemplary method is provided for protecting a sealing surface of a sealing portion of a medical fluid fitting, using a protective cap. The sealing surface is configured to form a fluid tight seal with a mating part so that fluid may pass through the medical fluid fitting. The method includes positioning a cap thread provided on a body of the protective cap in coaxial alignment with a fitting thread provided on the medical fluid fitting. The cap thread is threadedly engaged with the fitting thread to releasably couple the protective cap with the medical fluid fitting. The cap thread frictionally contacts the fitting thread to retain the protective cap in coupling engagement with the medical fluid fitting. The sealing portion of the medical fluid fitting is peripherally surrounded by the protective cap such that no portion of the protective cap contacts the sealing surface.

Various additional features and advantages of the invention will become more apparent to those of ordinary skill in the art upon review of the following detailed description of the illustrative embodiments taken in conjunction with the accompanying drawings.

DETAILED DESCRIPTION

Figure 1A:
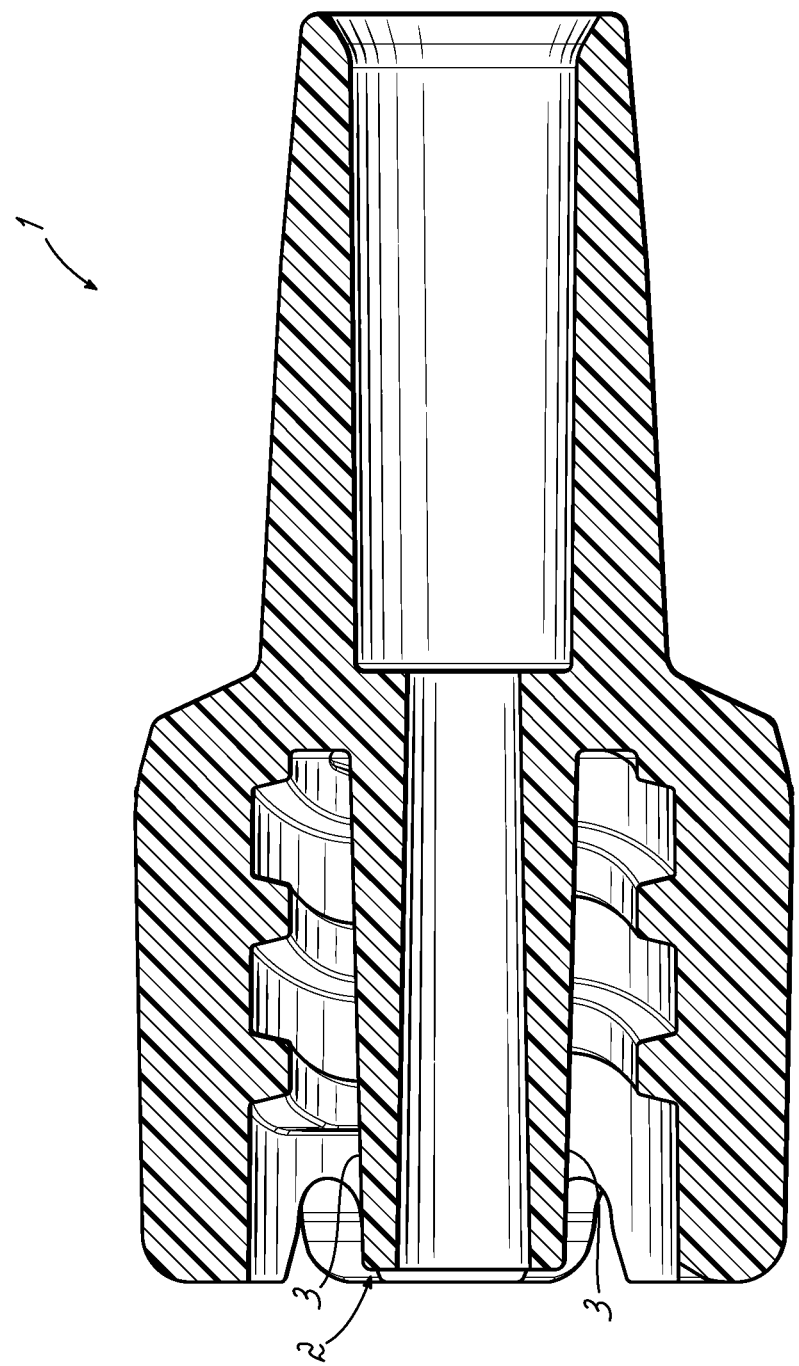
FIG. 1A is a cross-sectional view showing a known male medical fluid fitting.
Figure 1B:
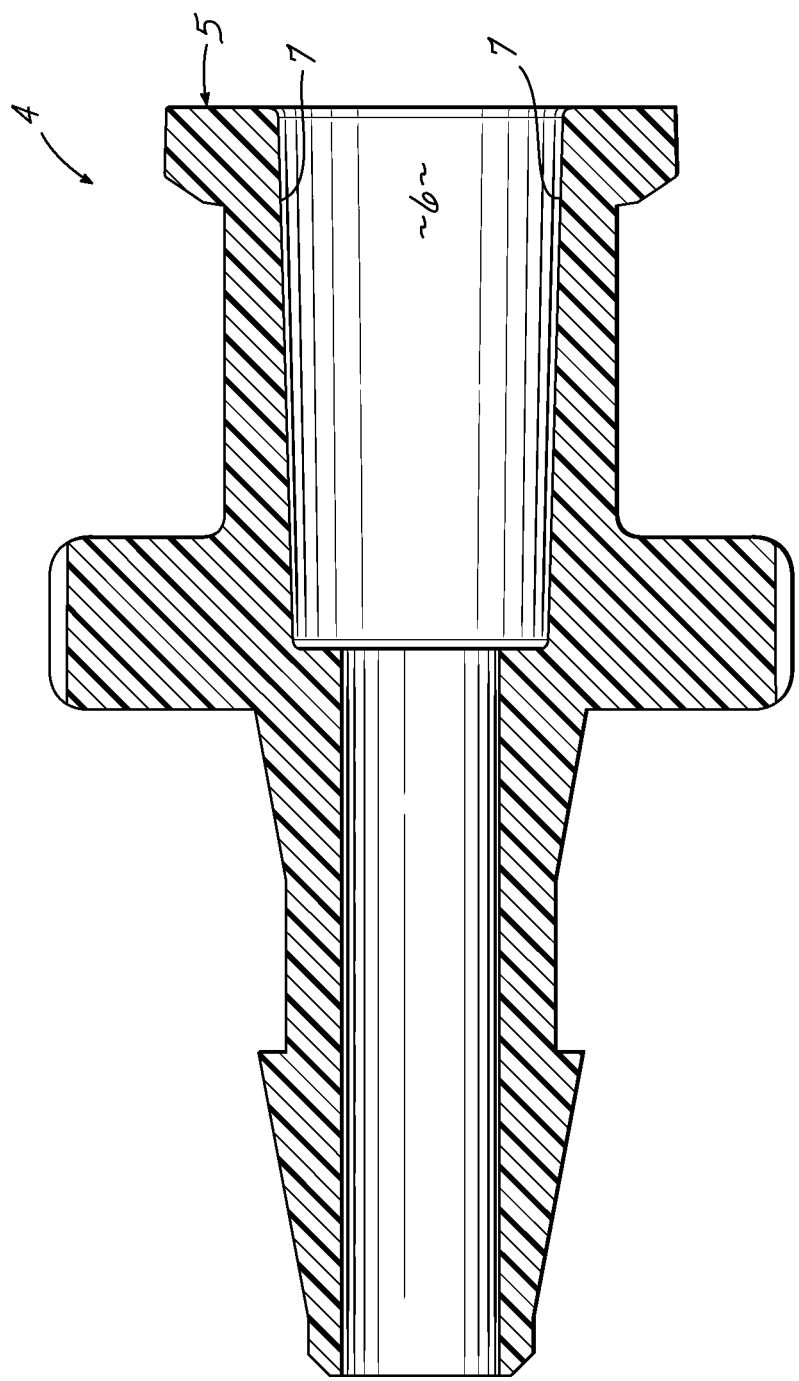
FIG. 1B is a cross-sectional view showing a known female medical fluid fitting.
Figure 2:
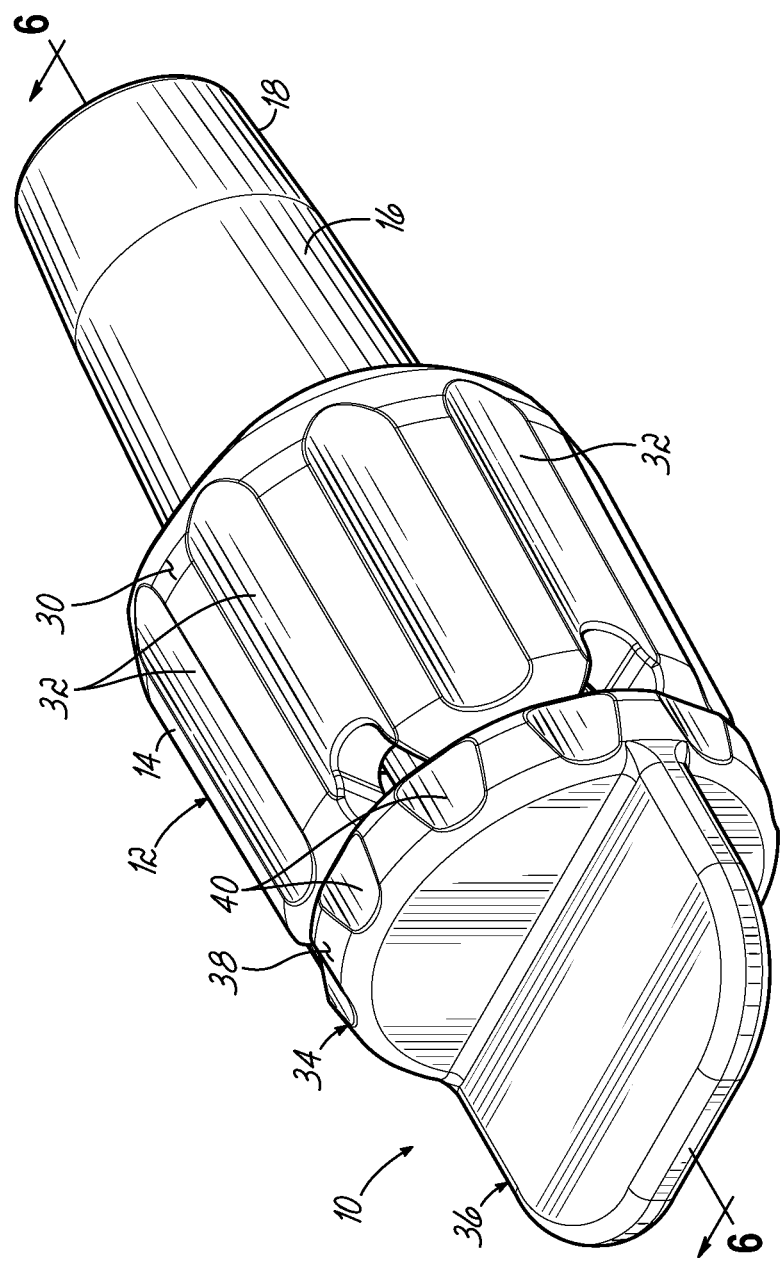
FIG. 2 is a perspective view showing a first embodiment of a male protective cap, assembled with a male medical fluid fitting.

Referring to FIGS. 2-7, a first exemplary embodiment of a male protective cap 10 in accordance with the principles of the invention is shown. The male protective cap 10 is adapted for use with a male medical fluid fitting 12 configured to convey fluids therethrough. As shown in FIG. 2, the male fluid fitting includes a collar 14 and a stem 16 extending axially from the collar 14. The stem 16 is configured to be coupled to a medical conduit (not shown), such as a tubing, for forming a fluid-tight seal with the medical conduit so that fluid may pass through the conduit and into the fluid fitting 12. The stem 16 may include a tapered portion 18 for facilitating insertion of the stem into the medical conduit. The stem 16 may additionally include any suitable retention features, such as a barb (not shown), for retaining the stem 16 in coupling engagement with a medical conduit.

Figure 3:
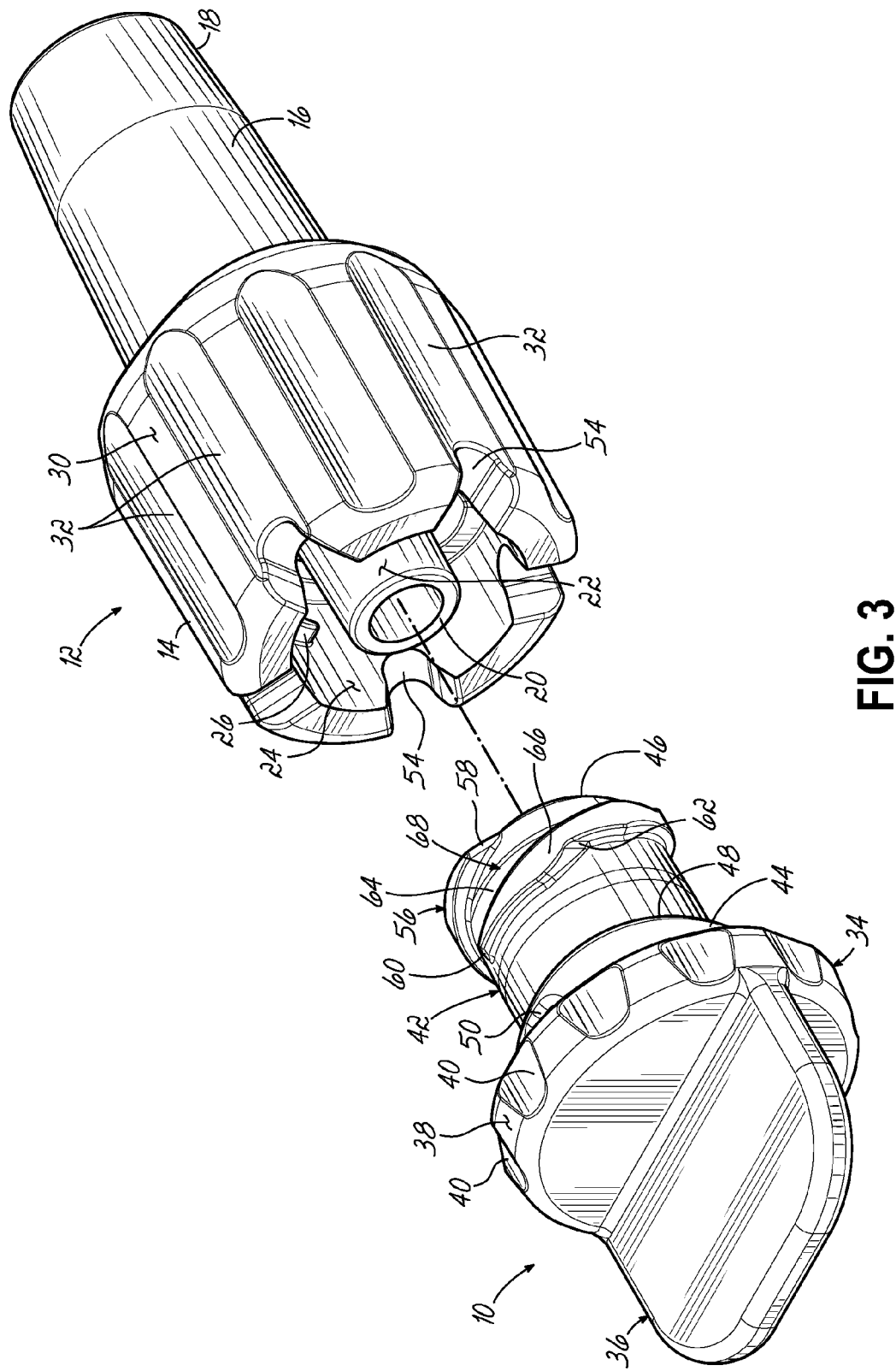
FIG. 3 is a perspective, disassembled view showing the male protective cap and male medical fluid fitting of FIG. 2.
Figure 4:
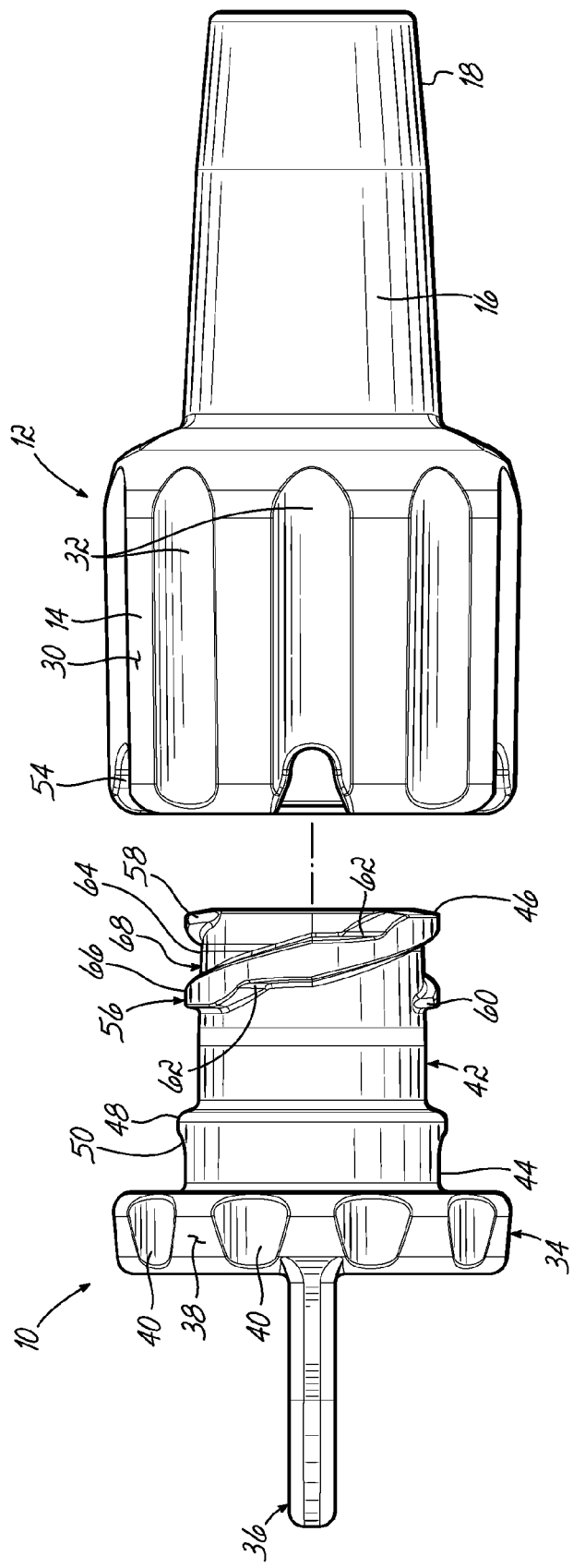
FIG. 4 is a side, disassembled view showing the male protective cap and male medical fluid fitting of FIG. 2.
Figure 5:
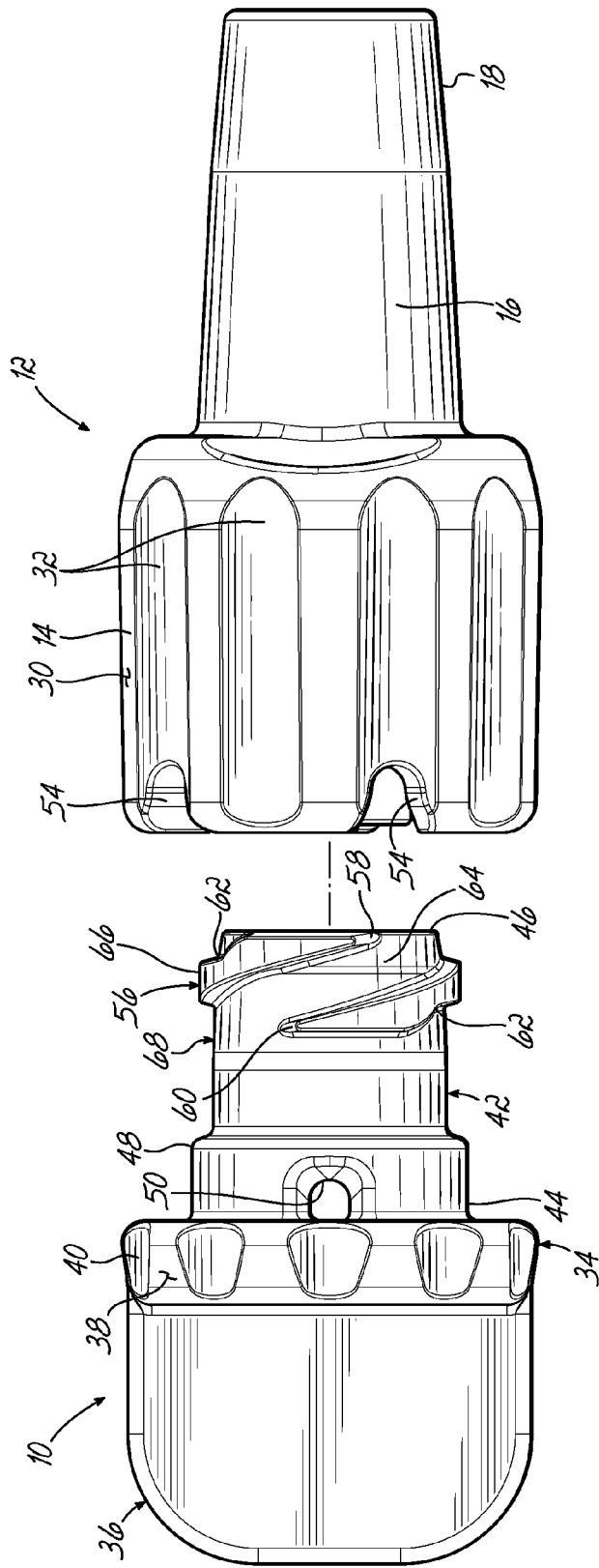
FIG. 5 is a top, disassembled view showing the male protective cap and male medical fluid fitting of FIG. 2.

Referring to FIGS. 3-5, additional features of the male protective cap 10 and the male fluid fitting 12 are shown. The male fluid fitting 12 includes a male sealing portion 20, shown in the form of a tapered, nozzle-like protrusion, extending along a longitudinal axis of the male fluid fitting 12. The male sealing portion 20 defines a sealing surface 22, shown in the form of a tapered sealing surface, that is configured to form a fluid-tight seal with a mating female component (not shown). The sealing surface 22 may include a luer taper or any other suitable taper, for example. In this regard, although the male fluid fitting 12 is shown as having a tapered sealing surface 22, persons skilled in the art will appreciate that various embodiments of male protective caps in accordance with the principles of the invention may be adapted as appropriate for male fluid fittings having various types of sealing surfaces other than tapered sealing surfaces.

Figure 7:
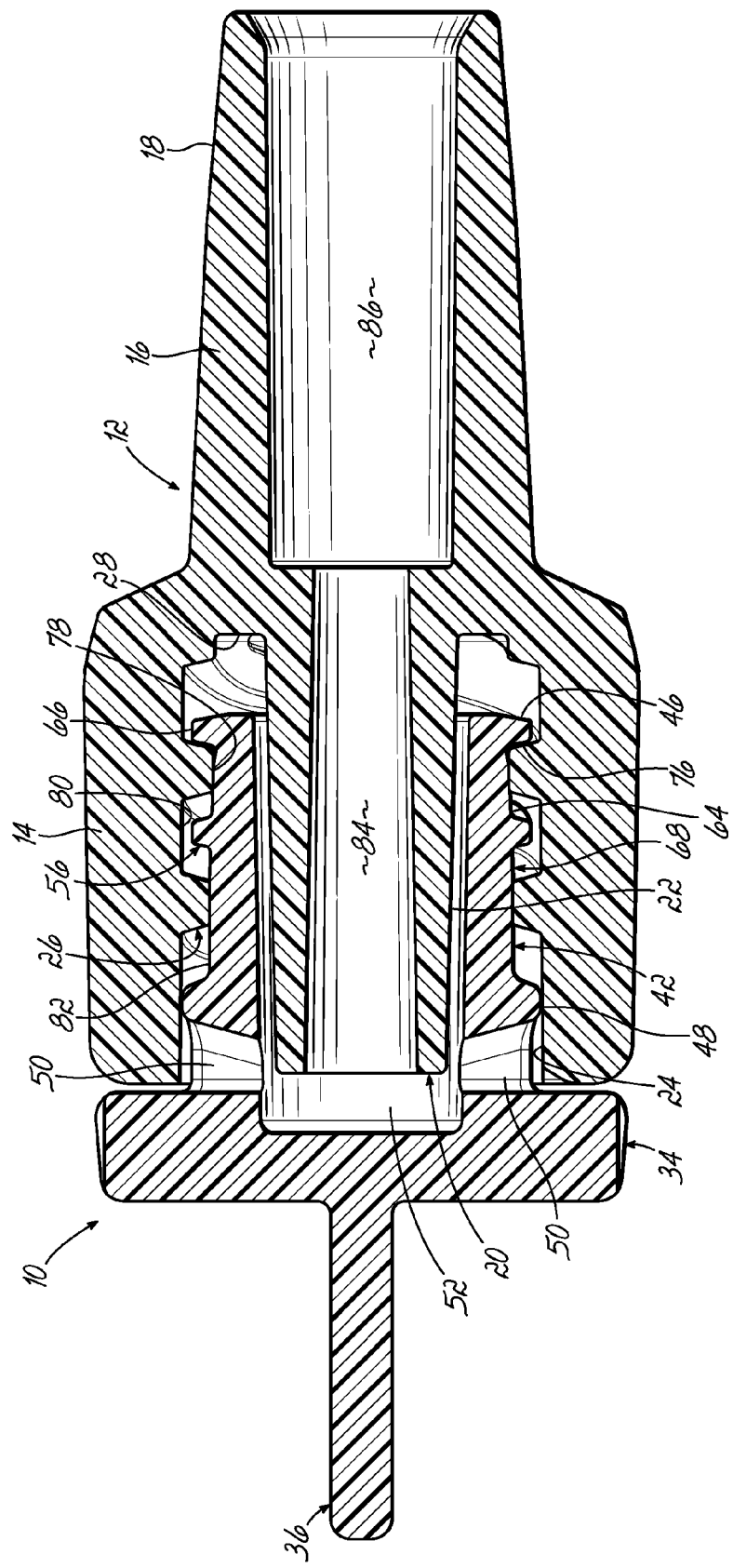
FIG. 7 is a cross-sectional view taken along line 6-6 of FIG. 2, showing the male protective cap assembled with the male medical fluid fitting.

The collar 14 of the male fluid fitting 12 circumferentially surrounds the male sealing portion 20 and includes a radially inner surface 24 that supports a helical fitting thread 26 which extends axially toward a base surface 28 of the sealing portion 20 (see FIG. 7). The fitting thread 26 is configured to threadedly engage a corresponding thread of a mating component (not shown). Additionally, the fitting thread 26 may be an overhauling thread that is configured to de-thread and separate from the corresponding thread of a mating component when opposing axial forces are applied to the fluid fitting 12 and the mating component. A radially outer surface 30 of the collar 14 may include one or more gripping features, shown in the form of longitudinal grooves 32, for aiding a user in gripping the fluid fitting during use, for example.

The male protective cap 10, according to the embodiment shown, includes a base 34 and a tab 36 extending outwardly from the base 34 for facilitating manipulation of the protective cap 10 relative to the male fluid fitting 12. A radially outer surface 38 of the base 34 may include one or more gripping features, shown in the form of notches 40, which may generally correspond in width and depth to the grooves 32 on the fluid fitting 12, and may aid a user in gripping the protective cap 10 during use.

As shown in FIGS. 3-5, a body 42 of the male protective cap 10 extends axially from the base 34 and includes a proximal end 44 and a distal end 46. The proximal end 44 includes a shoulder 48, which may include one or more cap vents 50 that extend radially through the shoulder 48 into a bore 52, shown in FIG. 6, and cooperate with one or more fitting vents 54 formed on the fluid fitting 12, as described in greater below. The cap body 42 includes a helical cap thread 56 that extends axially toward the distal end 46. The cap thread 56 is configured to be threadedly engaged with the fitting thread 26 for releasably coupling the protective cap 10 with the fluid fitting 12. As shown, the cap thread 56 may be formed with a width that tapers circumferentially at a thread start 58 and at a thread end 60. Additionally, the cap thread 56 may be formed with one or more cut-out features 62, which may be included for facilitating removal of the cap 10 from a mold during an injection-molding process during manufacture, for example.

As described below, protective caps of various embodiments in accordance with the principles of the invention include a tapered engagement surface defined by one of a root or a crest of the cap thread. The tapered engagement surface extends helically and tapers axially relative to a longitudinal axis of the cap body and is configured to frictionally engage a corresponding fitting thread on a medical fluid fitting for retaining the protective cap in coupling engagement with the medical fluid fitting. In the embodiment shown in FIGS. 2-7, the cap thread 56 of the male protective cap 10 includes a thread root 64, a thread crest 66, and a tapered engagement surface 68 defined by the thread root 64.

Figure 6:
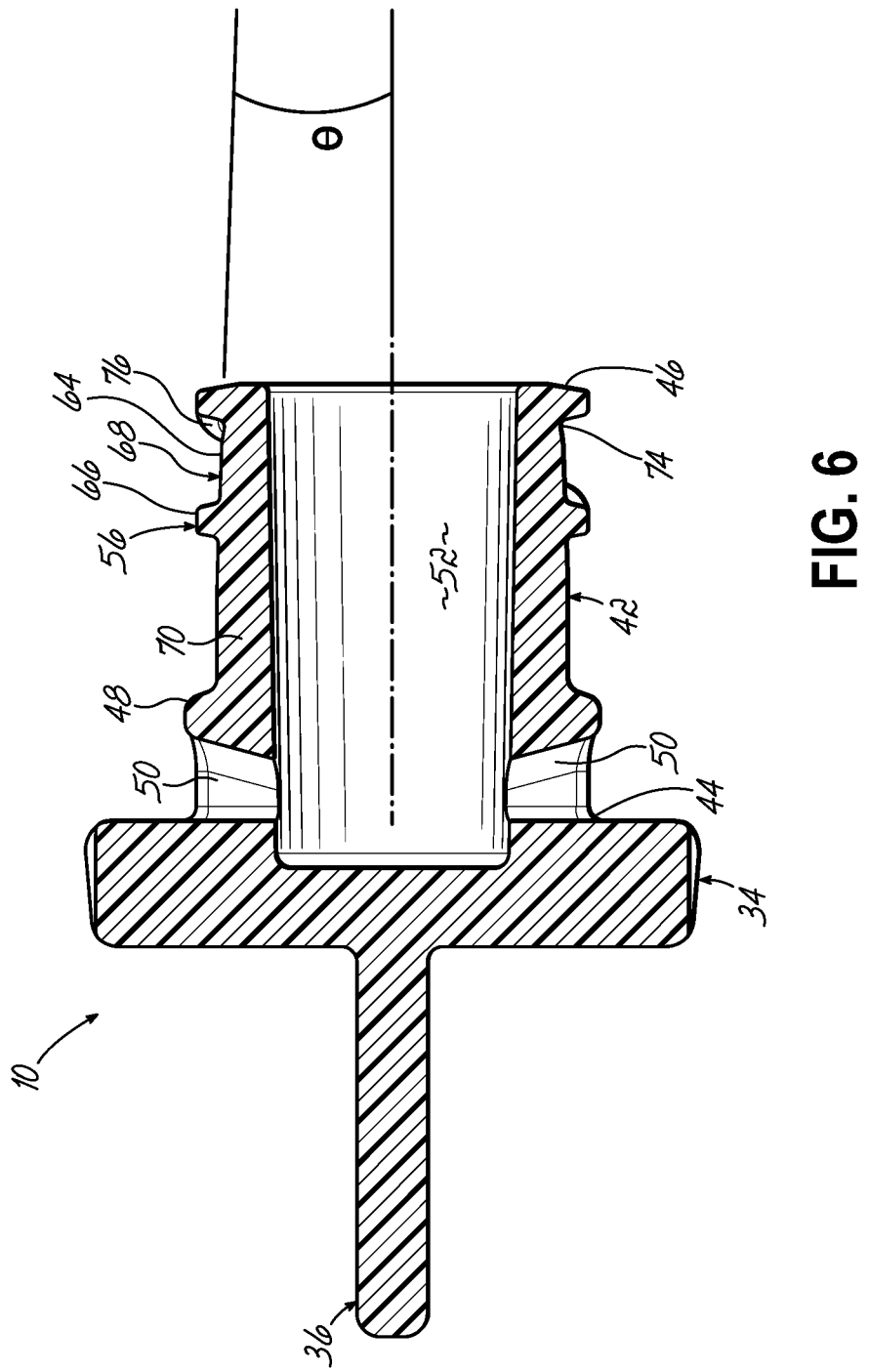
FIG. 6 is a cross-sectional view taken along line 6-6 of FIG. 2, showing the male protective cap.

As best shown in FIG. 6, the body 42 of the male protective cap 10 includes a cylindrical wall 70 defining the bore 52 that extends axially from the distal end 46 to the proximal end 44 and into the base 34. As described above, the tapered engagement surface 68 is defined by the root 64 of the cap thread 56 and extends helically and tapers axially relative to the longitudinal axis of the cap body 42. The tapered surface 68 tapers from a large diameter at the proximal end 44 of the cap body 42 to a smaller diameter at the distal end 46 of the cap body 42. In this regard, the tapered surface 68 may extend proximally beyond the thread end 60, up to the shoulder 48. In this embodiment, an outer diameter defined by the crest 66 of the cap thread 56 remains substantially constant along an axial length of the cap thread 56. Accordingly, a thread height of the cap thread 56, defined by a radial distance between the thread root 64 and the thread crest 66, decreases proximally. Additionally, the tapered surface 68 may include a circumferential lead-in feature 74 at the distal end 46 for facilitating initial threaded engagement of the cap thread 56 with the fitting thread 26, as shown in FIG. 7.

The tapered engagement surface 68 tapers distally relative to the longitudinal axis of the cap body 42. In one embodiment, the tapered surface 68 tapers with an included taper angle of approximately three degrees to approximately six degrees, and thus with a non-included taper angle θ of approximately 1.5 degrees to approximately three degrees, as shown in FIG. 6. Other embodiments of protective caps in accordance with the principles of the invention, including those shown and described herein, may also include tapered engagement surfaces that taper relative to a longitudinal axis of the corresponding cap body with an included taper angle of approximately three degrees to approximately six degrees, and a non-included taper angle θ of approximately 1.5 degrees to approximately three degrees.

As shown in FIG. 7, the male protective cap 10 may be releasably coupled with the male fluid fitting 12 such that the cap body 42 peripherally surrounds the male sealing portion 20 without contacting the sealing surface 22. In this manner, the protective cap 10 may shield the sealing surface 22 from unwanted contact with ambient elements and conditions. More specifically, the externally-threaded cap body 42 is coaxially aligned with the internally-threaded fitting collar 14 and inserted therein such that the male sealing portion 20 is received within the bore 52 of the cap body 42. The protective cap 10 is rotated about its longitudinal axis, for example using the tab 36, so that cap thread 56 threadedly engages the fitting thread 26. As shown, the shoulder 48 of the cap body 42 may contact the radially inner surface 24 of the collar 14 to promote axial alignment of the protective cap 10 with the fluid fitting 12.

As the male protective cap 10 is rotated into increased threaded engagement with the male fluid fitting 12, a trailing side 76 of the cap thread 56 engages the fitting thread 26 to advance the distal end 46 of the cap body 42 axially toward the base surface 28 of the male sealing portion 20. Simultaneously, the tapered engagement surface 68 defined by the root 64 of the cap thread 56 exerts a radial, outwardly-directed compressive force on, and thereby frictionally contacts, a thread crest 78 of the fitting thread 26. In one embodiment, as shown, no portion of the cap thread 56 contacts a thread root 80 of the fitting thread 26, such that a radial gap is formed between the crest 66 of the cap thread 56 and the root 80 of the fitting thread 26. The radial compressive force exerted on the fitting thread 26 by the tapered surface 68, for example by a proximal portion 82 thereof, increases progressively as threaded engagement of the cap thread 56 and the fitting thread increases 26.

In this manner, an interference fit is created between the cap thread 56 and the fitting thread 26, thereby retaining the protective cap 10 in coupling engagement with the fluid fitting 12. Accordingly, although the fitting thread 26 may be an overhauling-type thread, as described above, the threaded engagement between the fitting thread 26 and the cap thread 56 may be a non-overhauling-type engagement. Thus, the male protective cap 10 and the female fluid fitting 12 do not de-thread and separate from each other upon application of opposing axial forces on the protective cap 10 and the fluid fitting 12.

As shown in FIG. 7, the male fluid fitting 12 includes a first bore 84 extending through the male sealing portion 20, and a second bore 86 extending through the stem 16, the first and second bores 84, 86 being connected in fluidic communication to define a fluid flow path for conveying fluids. In one embodiment, the cap vents 50 provided on the cap body 42 may extend and taper radially through the shoulder 48 and be arranged in fluidic communication with the cap bore 52. Accordingly, when the protective cap 10 is coupled with the fluid fitting 12, as shown in FIG. 7, the cap vents 50 are positioned in fluidic communication with the fluid flow path on one side and with an ambient environment on another side, via the fitting vents 54 (see FIGS. 3-5). In this manner, gasses residing within the fluid flow path may be released through the cap vents 50 and the fitting vents 54 to an ambient environment.

Figure 8:
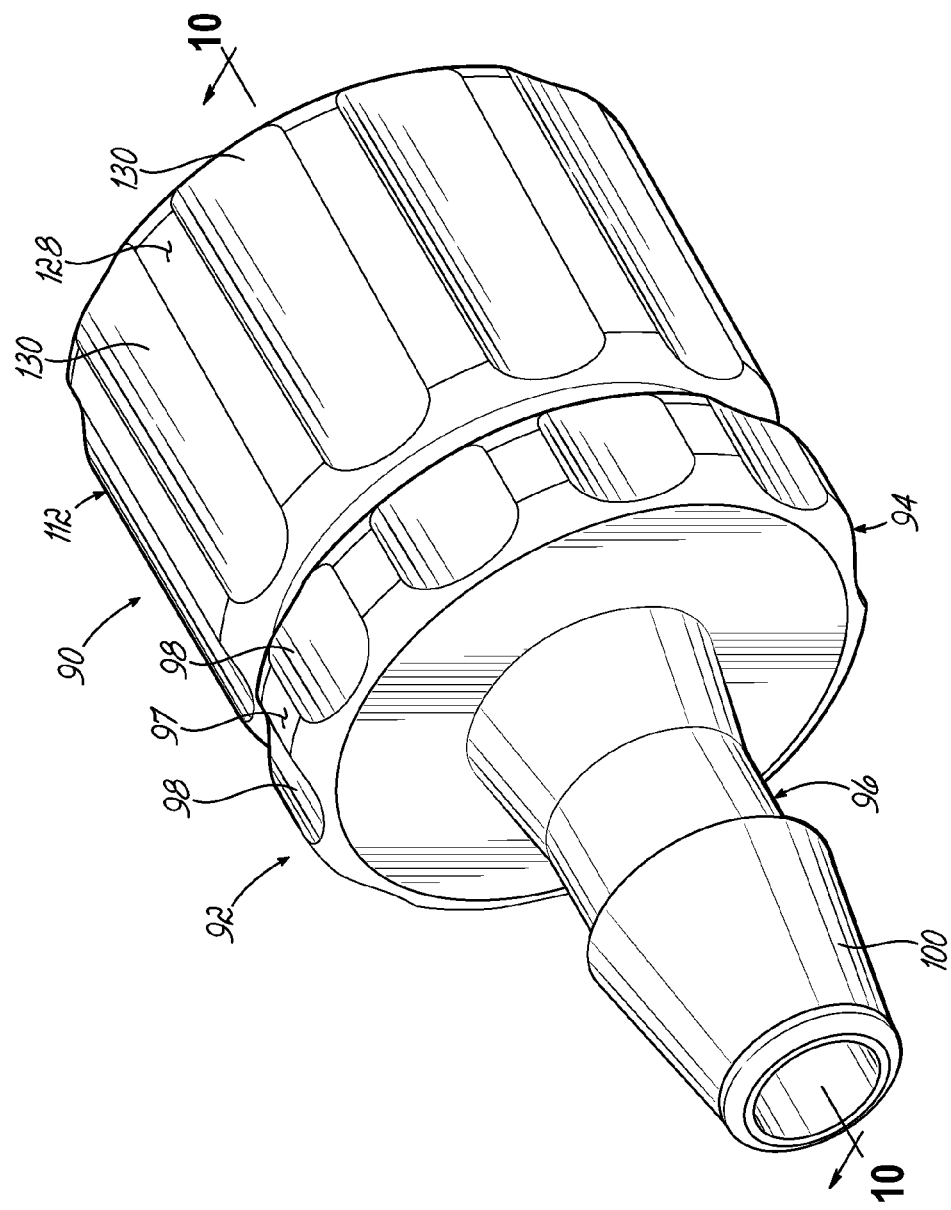
FIG. 8 is a perspective view showing a first embodiment of a female protective cap, assembled with a female medical fluid fitting.
Figure 9:
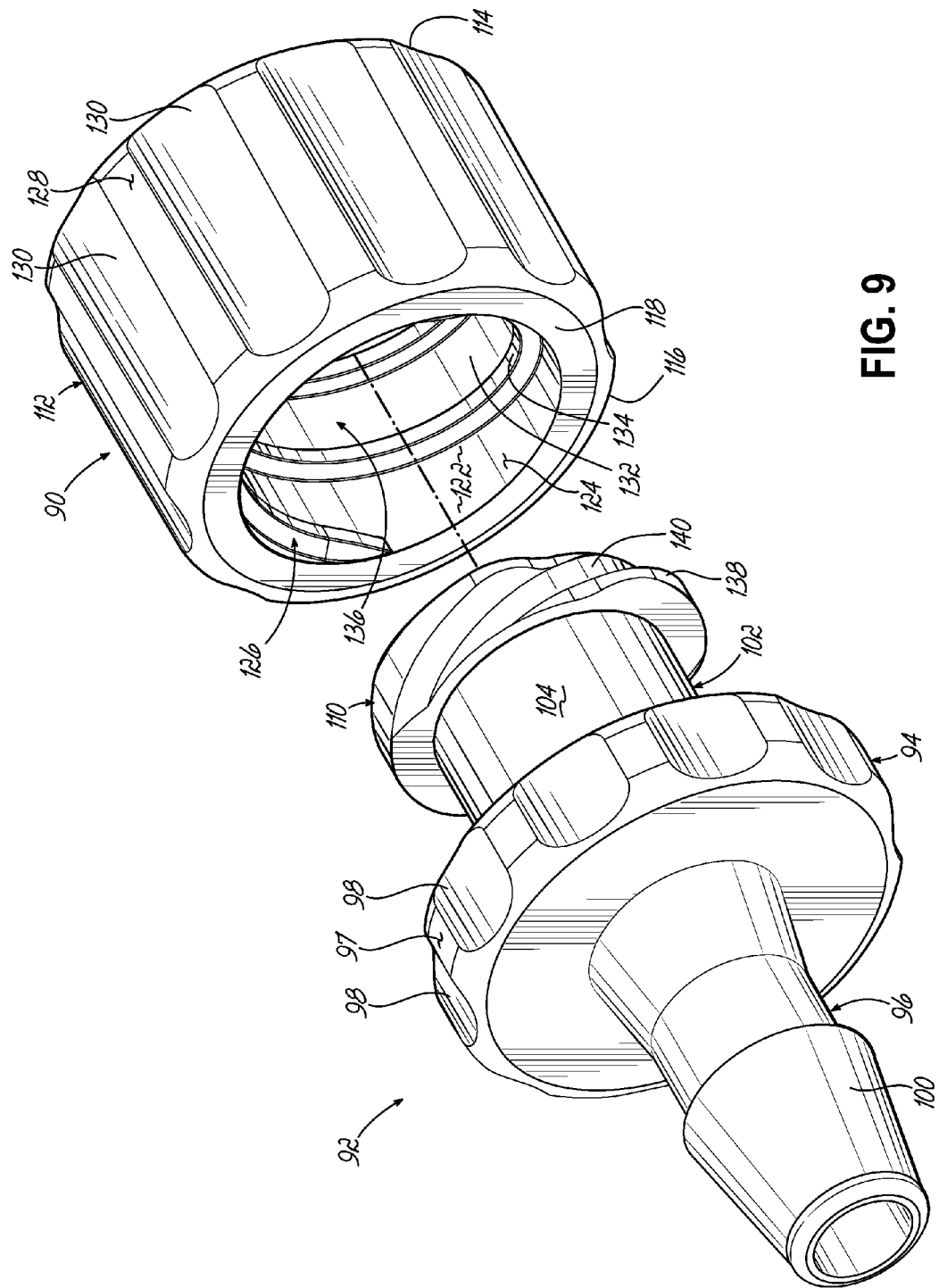
FIG. 9 is a perspective, disassembled view showing the female protective cap and female medical fluid fitting of FIG. 8.

Referring to FIGS. 8-11, a first exemplary embodiment of a female protective cap 90 in accordance with the principles of the invention is shown. The female protective cap 90 is adapted for use with a female medical fluid fitting 92 configured to convey fluids therethrough. As shown in FIGS. 8 and 9, the female fluid fitting 92 includes a base 94 and a stem 96 extending axially from the base 94. A radially outer surface 97 of the base 94 may include one or more gripping features, shown in the form of notches 98, for aiding a user in gripping the fluid fitting 92 during use. The stem 96 is configured to be coupled to a medical conduit (not shown), such as a tubing, for forming a fluid-tight seal with the medical conduit so that fluid may pass through the conduit and into the fluid fitting. The stem 96 may include a barb 100 for retaining the stem 96 in coupling engagement with the medical conduit and forming a fluid-tight seal with the conduit.

Figure 11:
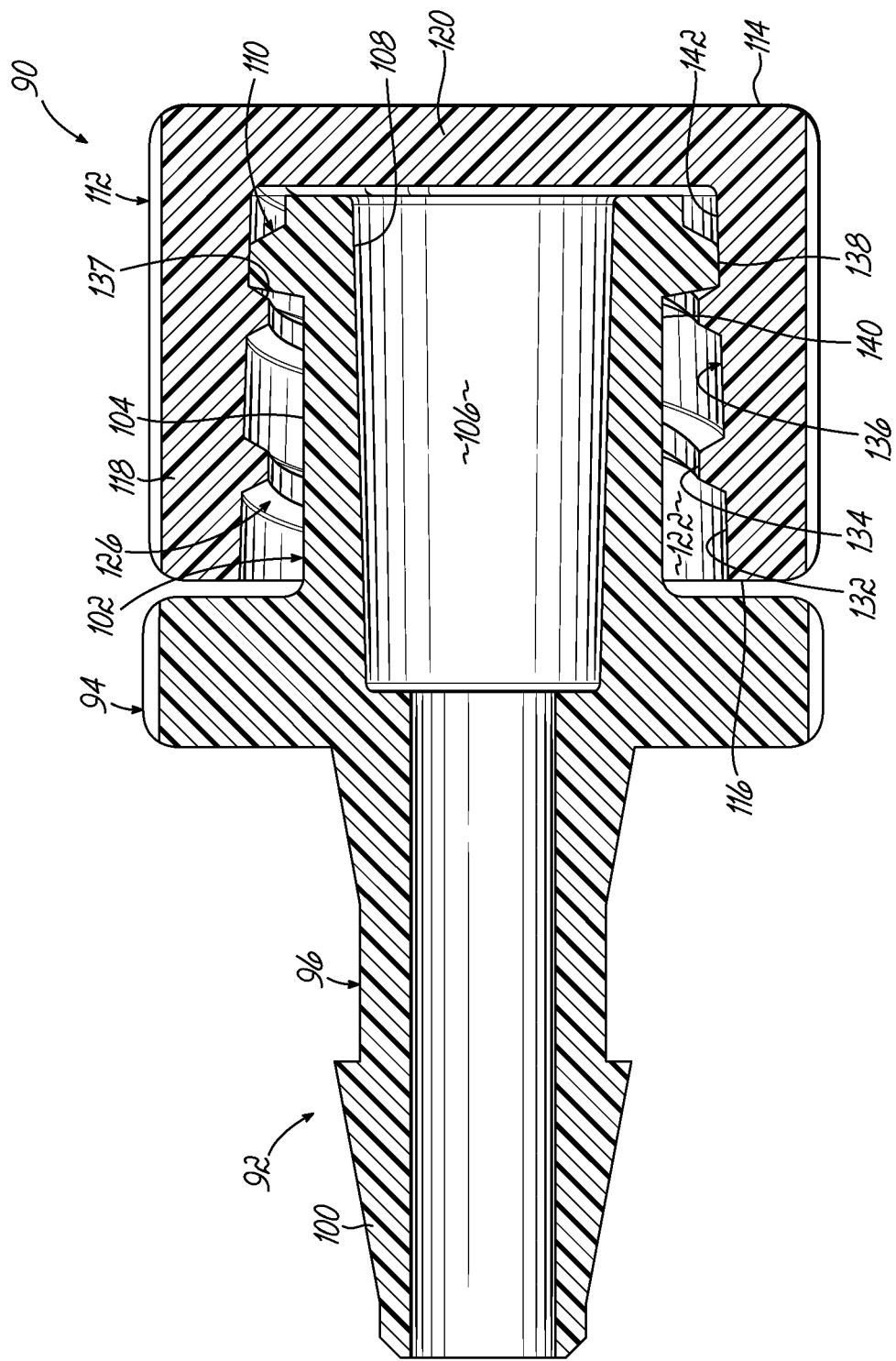
FIG. 11 is a cross-sectional view taken along line 10-10 of FIG. 8, showing the female protective cap assembled with the female medical fluid fitting.

As best shown in FIGS. 9 and 11, the female fluid fitting 92 includes a female sealing portion 102 extending axially from the base 94. The female sealing portion 102 includes a circumferential wall 104 and a fitting socket 106 extending along a longitudinal axis of the fluid fitting 92 and defining a sealing surface 108, shown in the form of a tapered sealing surface. The sealing surface 108 is configured to form a fluid-tight seal with a mating male component (not shown), and may include a luer taper or any other suitable taper, for example. As described above in connection with the male fluid fitting 12 of FIGS. 2-7, various embodiments of female protective caps in accordance with the principles of the invention may be adapted as appropriate for female fluid fittings having various types of sealing surfaces other than tapered sealing surfaces.

A radially outer portion of the circumferential wall 104 of the female sealing portion 102 includes a helical fitting thread 110 extending axially. The fitting thread 110 is configured to threadedly engage a corresponding thread of a mating component (not shown). Additionally, the fitting thread 110 may be an overhauling-type thread that it is configured to de-thread and separate from the corresponding thread of a mating component when opposing axial forces are applied to the mating component and the fluid fitting 92.

Figure 10:
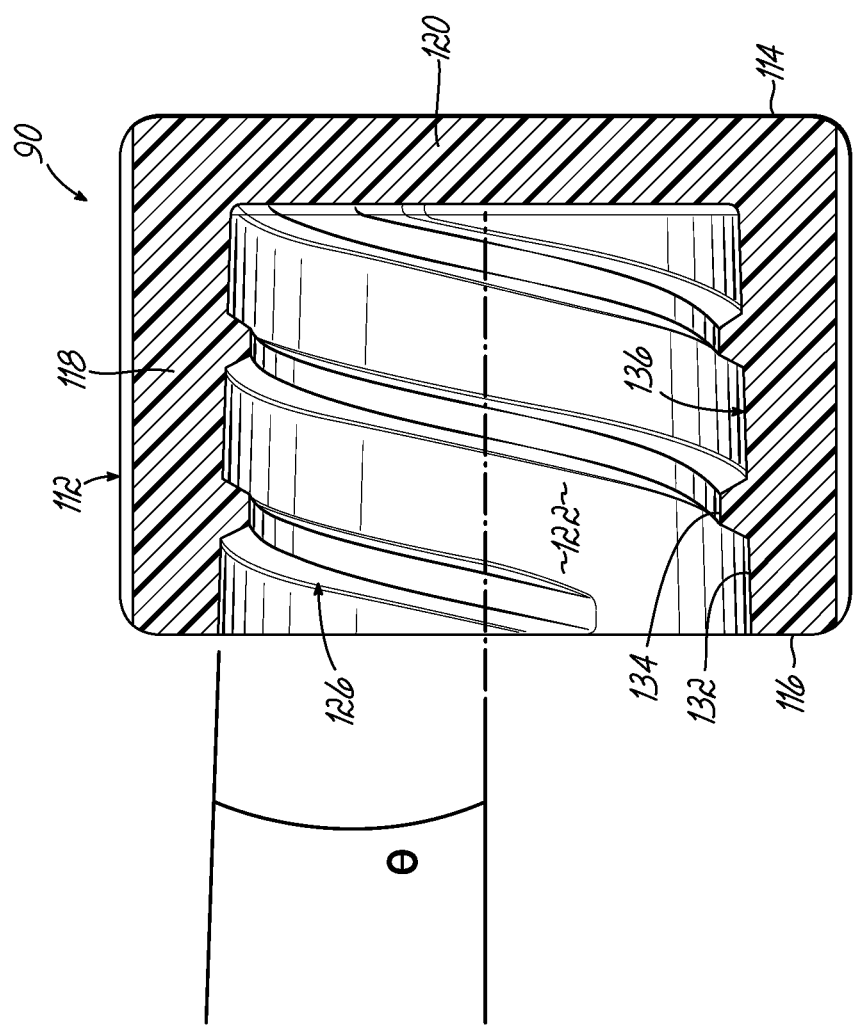
FIG. 10 is a cross-sectional view taken along line 10-10 of FIG. 8, showing the female protective cap.

As shown in FIGS. 9 and 10, the female protective cap 90 includes a body 112 having a proximal end 114 and a distal end 116. The body 112 includes a circumferential wall 118 that is integrally formed with an end wall 120 at the proximal end 114 and defines a cap socket 122 extending along a longitudinal axis of the body 112. A radially inner surface 124 of the circumferential wall 118 supports a helical cap thread 126 that extends axially from the distal end 116 toward the proximal end 114. As shown, the cap thread 126 may extend up to the end wall 120, for example. The cap thread 126 is configured to be threadedly engaged with the fitting thread 110 for releasably coupling the female protective cap 90 with the female fluid fitting 92, as described in greater detail below. In that regard, a radially outer surface 128 of the cap body 112 may include one or more gripping features, shown in the form of longitudinal grooves 130, for aiding a user in gripping the protective cap 90 when coupling the cap 90 with the fluid fitting 92, described in greater detail below.

In the embodiment shown, the cap thread 126 of the female protective cap 90 includes a thread root 132, a thread crest 134, and a tapered engagement surface 136 defined by the thread root 132. The tapered engagement surface 136 extends helically and tapers proximally relative to the longitudinal axis of the body 112. As shown, the tapered surface 136 tapers from a large diameter at the distal end 116 of the cap body 112 to a smaller diameter at the proximal end 114 of the cap body 112. In one embodiment, an inner diameter defined by the crest 134 of the cap thread 126 remains substantially constant along an axial length of the cap thread 126. Accordingly, a thread height of the cap thread 126, defined by a radial distance between the thread root 132 and the thread crest 134, decreases proximally.

Similar to the tapered engagement surface 68 of the male protective cap 10 of FIGS. 2-7, the tapered engagement surface 136 of the female protective cap 90 may taper with an included taper angle of approximately three degrees to approximately six degrees relative to the longitudinal axis of the cap body 112. Accordingly, as shown in FIG. 10, the tapered surface 136 may taper with a non-included taper angle θ of approximately 1.5 degrees to approximately three degrees relative to the cap body 112.

As shown in FIG. 11, the female protective cap 90 may be releasably coupled with the female fluid fitting 92 such that the cap body 112 peripherally surrounds the female sealing portion 102 without contacting the sealing surface 108. More specifically, the internally-threaded cap body 112 is coaxially aligned with the externally-threaded female sealing portion 102, which is received within the cap socket 122. The protective cap 90 is then rotated about its longitudinal axis, for example with the aid of grooves 130, to threadedly engage the cap thread 126 with the fitting thread 110.

As the female protective cap 90 is rotated into increased threaded engagement with the female fluid fitting 92, a trailing side 137 of the cap thread 126 engages the fitting thread 110 to advance the distal end 116 of the cap body 112 axially toward the base 94 of the female fluid fitting 92. Simultaneously, as similarly described above, the tapered engagement surface 136 defined by the root 132 of the cap thread 126 exerts a radial, inwardly-directed compressive force on, and thereby frictionally contacts, a crest 138 of the fitting thread 110. In one embodiment, as shown, no portion of the cap thread 126 contacts a thread root 140 of the fitting thread 110, such that a radial gap is formed between the crest 134 of the cap thread and the root 140 of the fitting thread 110. The radial compressive force exerted on the fitting thread 110 by the tapered surface 136, for example by a proximal portion 142 thereof, increases progressively as threaded engagement of the cap thread 126 and the fitting thread 110 increases.

In this manner, an interference fit is created between the cap thread 126 and the fitting thread 110, thereby retaining the female protective cap 90 in coupling engagement with the female fluid fitting 92. Accordingly, although the fitting thread 110 may be an overhauling-type thread, as described above, the threaded engagement between the fitting thread 110 and the cap thread 126 may be a non-overhauling-type engagement. Thus, the female protective cap 90 and the female fluid fitting 92 do not de-thread and separate from each other upon application of opposing axial forces on the protective cap 90 and the fluid fitting 92.

In summary, described above in connection with FIGS. 2-11 are first exemplary embodiments of male and female protective caps 10, 90, each including a tapered engagement surface 68, 136 defined by a root 64, 132 of the corresponding cap thread 56, 126. Now described below, in connection with FIGS. 12-17, are second exemplary embodiments of male and female protective caps 10a, 90a, each including a tapered engagement surface 68a, 136a defined by a crest 66a, 134a of the corresponding cap thread 56a, 126a.

Figure 12:
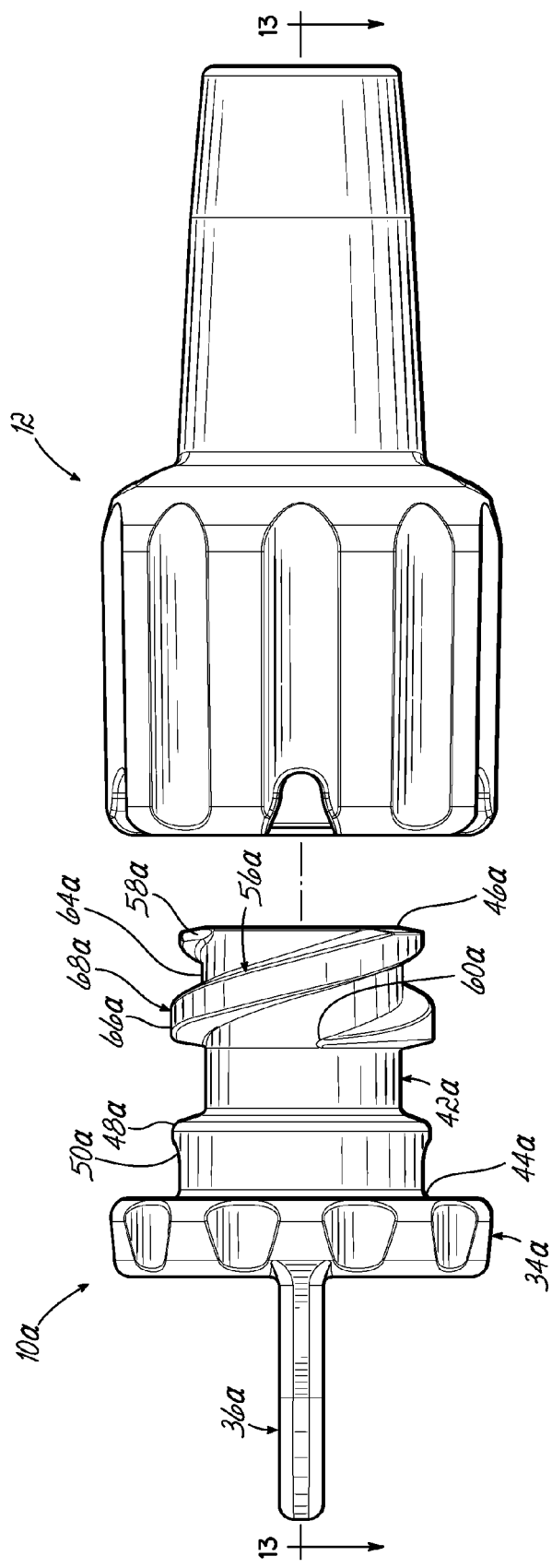
FIG. 12 is a side view showing a second embodiment of a male protective cap, disassembled from a male medical fluid fitting.
Figure 13:
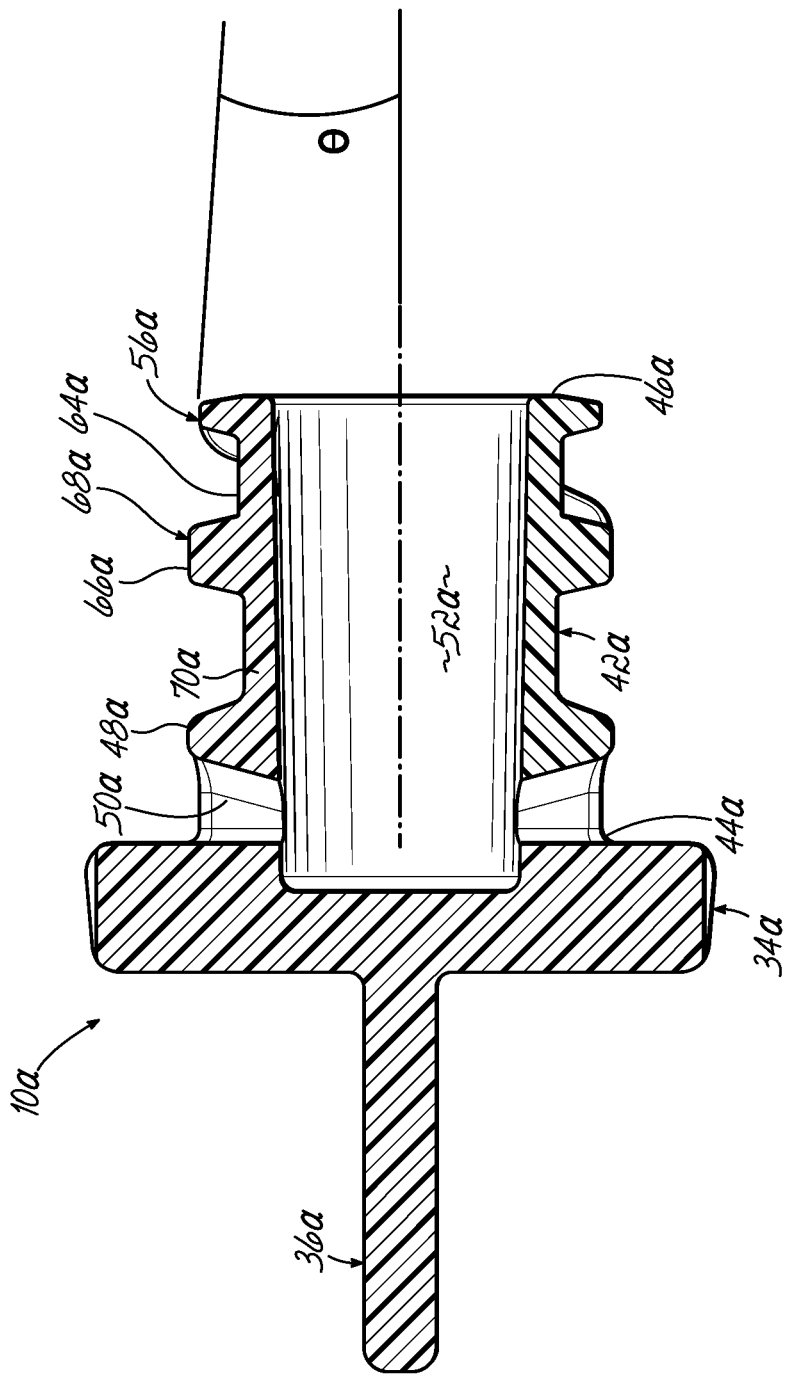
FIG. 13 is a cross-sectional view taken along line 13-13 of FIG. 12, showing the male protective cap.
Figure 14:
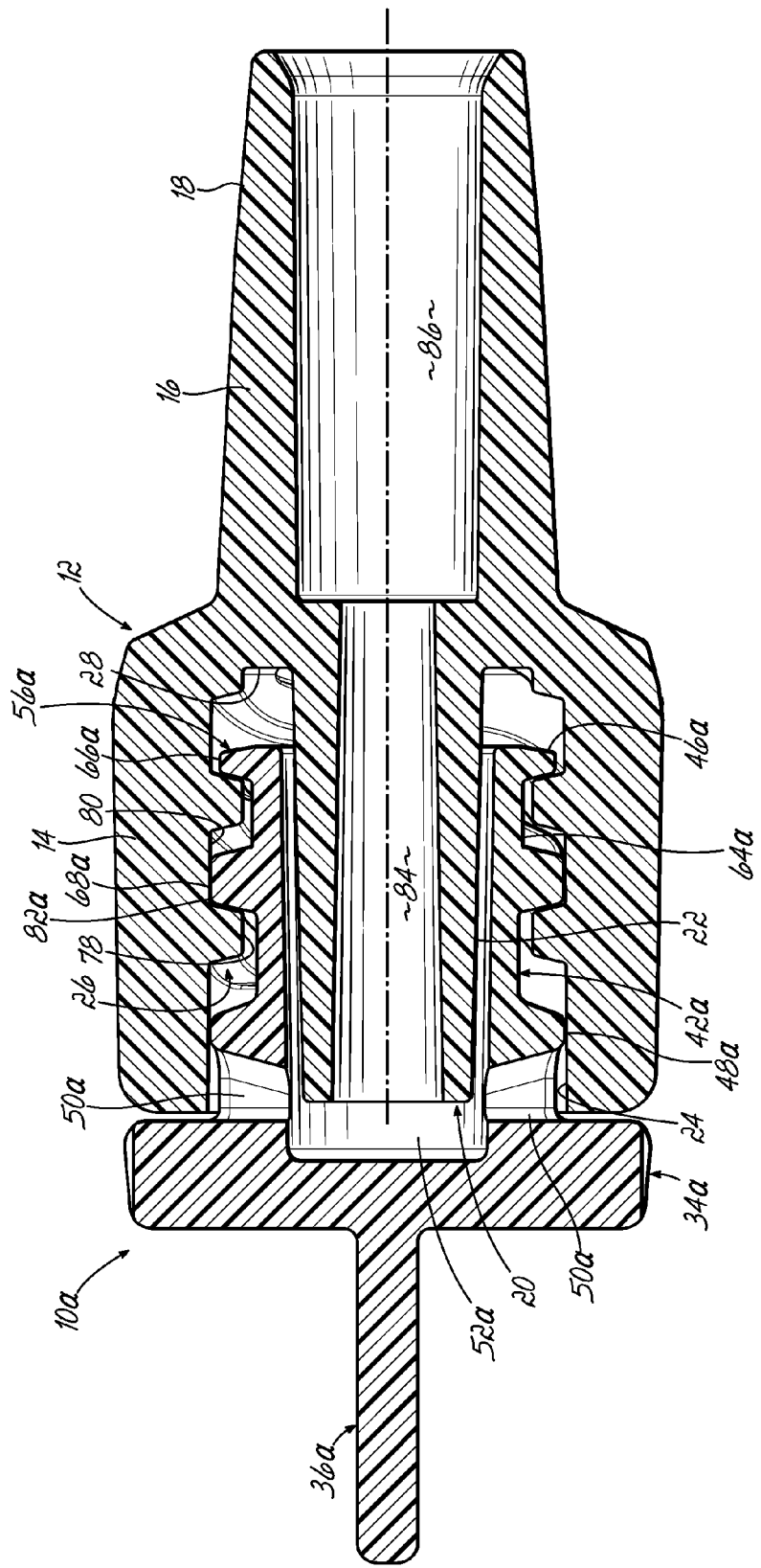
FIG. 14 is a cross-sectional view taken along line 13-13 of FIG. 12, showing the male protective cap assembled with the male medical fluid fitting.

Referring to FIGS. 12-14, a second exemplary embodiment of a male protective cap 10a in accordance with the principles of the invention is shown, for which similar reference numerals refer to similar features shown in FIGS. 2-7. The male protective cap 10a may be adapted for use with the male medical fluid fitting 12, for example. As described above, persons skilled in the art will appreciate that the male protective cap 10a may be modified as appropriate for use with male medical fluid fittings having various types of sealing surfaces, including tapered sealing surfaces.

As shown in FIGS. 12 and 13, a body 42a of the male protective cap 10a includes a helical cap thread 56a having a thread root 64a, a thread crest 66a, and a tapered engagement surface 68a defined by the thread crest 66a. An outer diameter defined by the crest 66a of the cap thread 56a increases proximally while a diameter defined by the root 64a of the cap thread 56a remains substantially constant along the axial length of the cap thread 56a. Accordingly, a thread height of the cap thread 56a, defined by a radial distance between the thread root 64a and the thread crest 66a, increases proximally.

Similar to the male cap 10 shown in FIGS. 2-7, the tapered engagement surface 68a of male cap 10a tapers distally relative to the longitudinal axis of the cap body 42a. In one embodiment, the tapered surface 68a tapers with an included taper angle of approximately three degrees to approximately six degrees, and with a non-included taper angle θ of approximately 1.5 degrees to approximately three degrees, as shown in FIG. 13.

As shown in FIG. 14, the male protective cap 10a may be releasably coupled to the male fluid fitting 12 such that the cap body 42a peripherally surrounds the male sealing portion 20 without contacting the sealing surface 22. In that regard, the male cap 10a may be coaxially aligned and coupled with the male fluid fitting 12 in a manner similar to that described above in connection with the male cap 10 shown in FIG. 7, such that the cap thread 56a threadedly engages the fitting thread 26.

In the embodiment shown in FIG. 14, as the male protective cap 10a is rotated into increased threaded engagement with the male fluid fitting 12, the tapered surface 68a defined by the crest 66a of the cap thread 56a exerts a radial, outwardly-directed compressive force on, and thereby frictionally contacts, the root 80 of the fitting thread 26. In one embodiment, as shown, no portion of the cap thread 56a contacts the crest 78 of the fitting thread 26, such that a radial gap is formed between the root 64a of the cap thread 56a and the crest 78 of the fitting thread 26. The radial compressive force exerted on the fitting thread 26 by the tapered surface 68a, for example by a proximal portion 82a thereof, increases progressively as threaded engagement of the cap thread 56a and the fitting thread 26 increases. In this manner, an interference fit is created between the cap thread 56a and the fitting thread 26, thereby retaining the protective cap 10a in coupling engagement with the fluid fitting 12.

Figure 15:
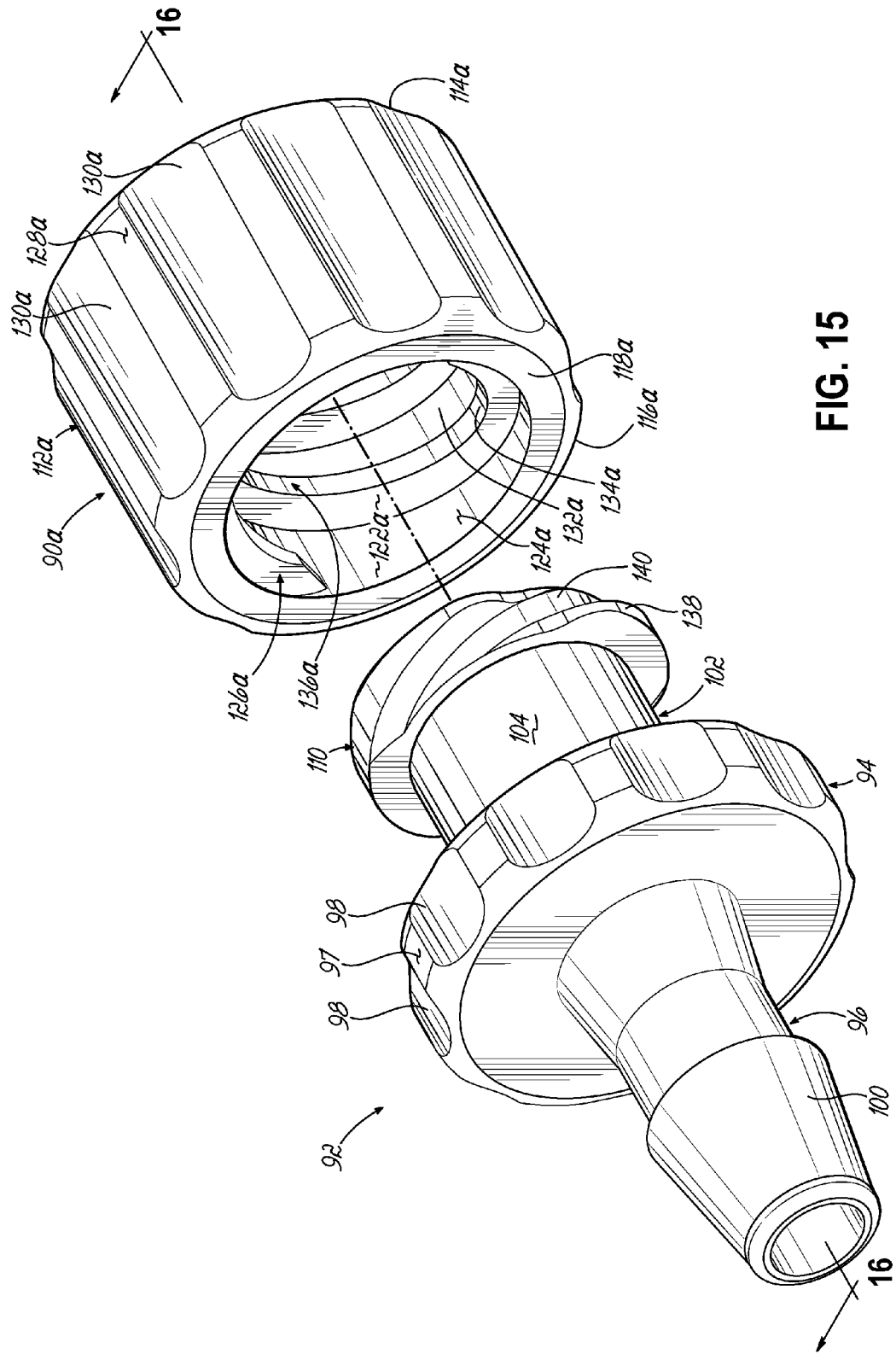
FIG. 15 is a perspective view showing a second embodiment of a female protective cap, disassembled from a female medical fluid fitting.
Figure 16:
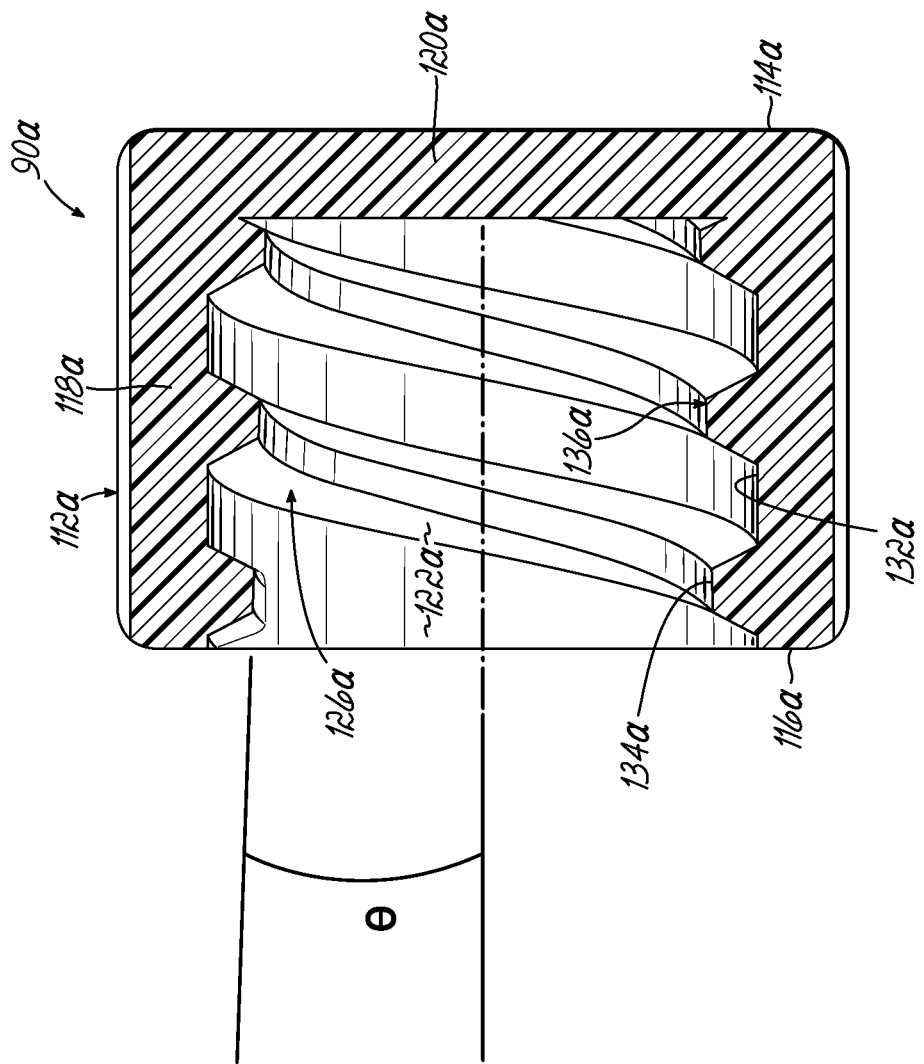
FIG. 16 is a cross-sectional view taken along line 16-16 of FIG. 15, showing the female protective cap.
Figure 17:
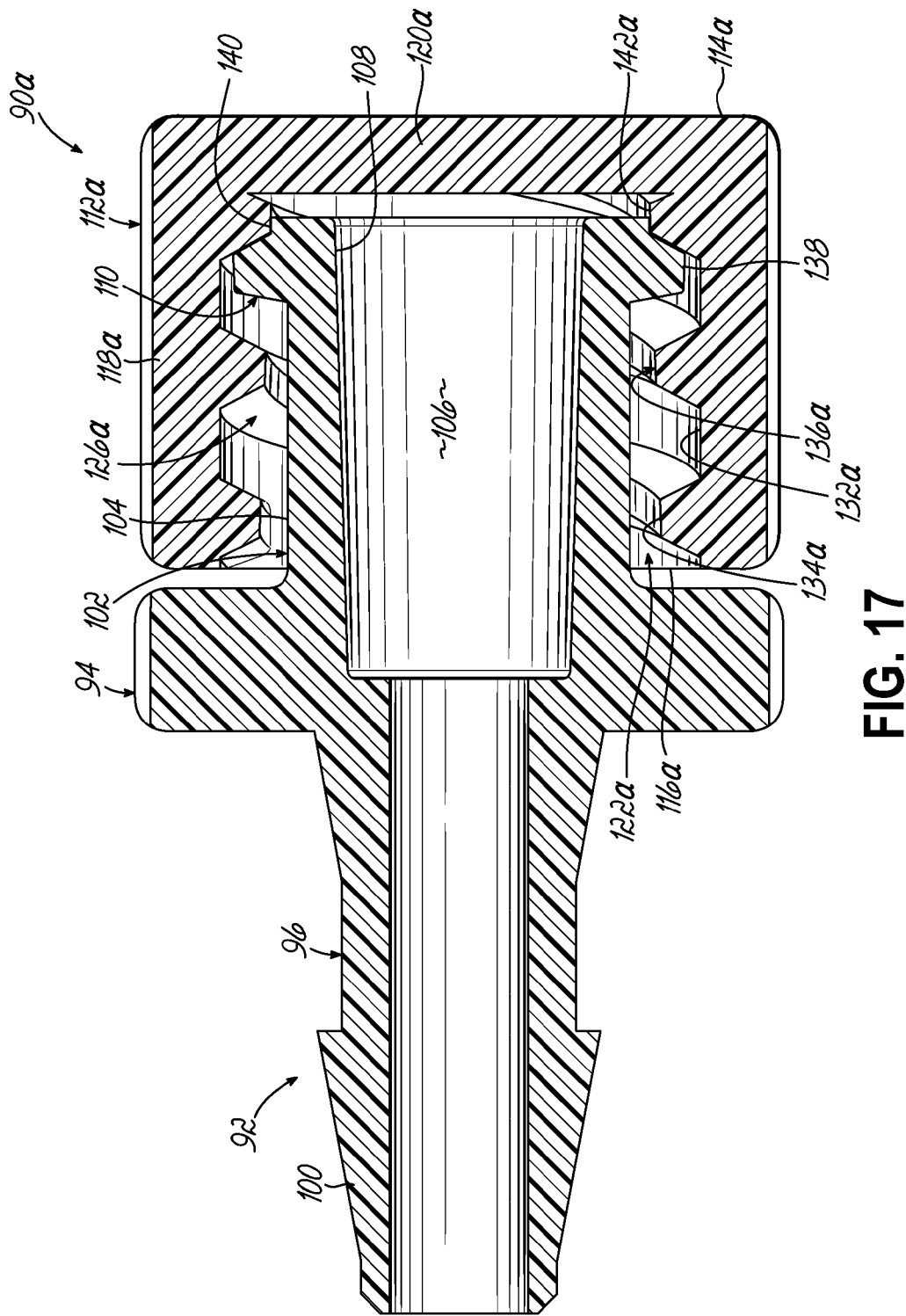
FIG. 17 is a cross-sectional view taken along line 16-16 of FIG. 15, showing the female protective cap assembled with the female medical fluid fitting.

Referring to FIGS. 15-17, a second exemplary embodiment of a female protective cap 90a in accordance with the principles of the invention is shown, for which similar reference numerals refer to similar features shown in FIGS. 8-11. The female protective cap 90a may be adapted for use with the female medical fluid fitting 92, for example. As described above, persons skilled in the art will appreciate that the female protective cap 90a may be modified as appropriate for use with female medical fluid fittings having various types of sealing surfaces, including tapered sealing surfaces.

As shown in FIGS. 15 and 16, a body 112a of the female protective cap 90a includes a circumferential wall 118a having a radially inner surface 124a that supports a helical cap thread 126a. The cap thread 126a includes a thread root 132a, a thread crest 134a, and a tapered engagement surface 136a defined by the thread crest 134a. The tapered surface 136a tapers from a large diameter at the distal end 116a of the cap body 112a to a smaller diameter at the proximal end 114a of the cap body 112a. In one embodiment, an inner diameter defined by the thread root 132a remains substantially constant along an axial length of the cap thread 126a. Accordingly, a thread height of the cap thread 126a, defined by a radial distance between the thread root 132a and the thread crest 134a, increases proximally.

Similar to the tapered engagement surface 136 of the female protective cap 90 shown in FIGS. 8-11, the tapered engagement surface 136a of female protective cap 90a tapers proximally relative to the longitudinal axis of the cap body 112a. In one embodiment, the tapered surface 136 tapers with an included taper angle of approximately three degrees to approximately six degrees, and with a non-included taper angle θ of approximately 1.5 degrees to approximately three degrees, as shown in FIG. 16.

As shown in FIG. 17, the female protective cap 90a may be releasably coupled to the female fluid fitting 92 such that the cap body 112a peripherally surrounds the female sealing portion 102 without contacting the sealing surface 108. In that regard, the female cap 90a may be coaxially aligned and coupled with the female fluid fitting 92 in a manner similar to that described above in connection with the female cap 90 shown in FIG. 11, such that the cap thread 126a threadedly engages the fitting thread 110.

In the embodiment shown in FIG. 17, as the female protective cap 90a is rotated into increased threaded engagement with the female fluid fitting 92, the tapered surface 136a defined by the crest 134a of the cap thread 126a exerts a radial, inwardly-directed compressive force on, and thereby frictionally contacts, the root 140 of the fitting thread 110. In one embodiment, as shown, no portion of the cap thread contacts the crest 138 of the fitting thread, such that a radial gap is formed between the root 132a of the cap thread 126a and the crest 138 of the fitting thread 110. The radial compressive force exerted on the fitting thread 110 by the tapered surface 136a, for example by a proximal portion 142a thereof, increases progressively as threaded engagement of the cap thread 126a and the fitting thread 110 increases. In this manner, an interference fit is created between the cap thread 126a and the fitting thread 110, thereby retaining the female protective cap 90a in coupling engagement with the female fluid fitting 92.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A protective cap for use with a medical fluid fitting configured to convey a fluid therethrough, the medical fluid fitting including a fitting thread and a sealing portion having a sealing surface for forming a fluid tight seal with a mating part, the protective cap comprising:
    a body having a proximal end and an open distal end;
    a cap thread provided on the body and extending axially, the cap thread configured to threadedly engage the fitting thread for releasably coupling the protective cap with the medical fluid fitting; and
    a tapered engagement surface defined by the cap thread and tapering axially relative to a longitudinal axis of the body, the tapered engagement surface configured to frictionally contact the fitting thread for retaining the protective cap in coupling engagement with the medical fluid fitting, the tapered engagement surface tapering from a larger diameter at the proximal end of the body to a smaller diameter at the open distal end of the body, the tapered engagement surface being defined by one of a root of the cap thread or a crest of the cap thread,
    wherein the protective cap is configured to peripherally surround the sealing portion such that no portion of the protective cap contacts the sealing surface when the protective cap is coupled with the medical fluid fitting.

2. The protective cap of claim 1, wherein the tapered engagement surface is defined by the root of the cap thread and is configured to frictionally contact a crest of the fitting thread without contacting a root of the fitting thread when the protective cap is coupled with the medical fluid fitting.

3. The protective cap of claim 2, wherein a thread height of the cap thread decreases proximally.

4. The protective cap of claim 1, wherein the tapered engagement surface is defined by the crest of the cap thread and is configured to frictionally contact a root of the fitting thread without contacting a crest of the fitting thread when the protective cap is coupled with the medical fluid fitting.

5. The protective cap of claim 4, wherein a thread height of the cap thread increases proximally.

6. The protective cap of claim 1, wherein the tapered engagement surface is formed with a non-included taper angle relative to the longitudinal axis of the body of the protective cap, the non-included taper angle ranging from approximately 1.5 degrees to approximately 3 degrees.

7. The protective cap of claim 1, wherein a radial force exerted by the cap thread on the fitting thread increases as threaded engagement of the cap thread with the fitting thread increases.

8. The protective cap of claim 1, wherein the medical fluid fitting includes a male fitting and the sealing portion includes an axial protrusion defining the sealing surface, and the body of the protective cap includes a bore sized to receive the axial protrusion such that the body peripherally surrounds the axial protrusion without contacting the sealing surface when the protective cap is coupled with the medical fluid fitting.

9. The protective cap of claim 1, wherein the medical fluid fitting includes a female fitting and the sealing portion includes a socket and a circumferentially extending wall defining the sealing surface, and the body of the protective cap is configured to peripherally surround the circumferentially extending wall without contacting the sealing surface when the protective cap is coupled with the medical fluid fitting.

10. The protective cap of claim 1, wherein the sealing surface of the medical fluid fitting includes a tapered sealing surface.

11. The protective cap of claim 9, wherein the sealing surface includes a luer taper.

12. A medical fluid fitting assembly, comprising:
a medical fluid fitting configured to convey a fluid therethrough, the medical fluid fitting including a fitting thread and a sealing portion having a sealing surface for forming a fluid tight seal with a mating part; and
a protective cap configured to protect the sealing surface of the medical fluid fitting, the protective cap including:
a body having a proximal end and an open distal end,
a cap thread provided on the body and extending axially, the cap thread configured to threadedly engage the fitting thread for releasably coupling the protective cap with the medical fluid fitting, and
a tapered engagement surface defined by the cap thread and tapering axially from a larger diameter at the proximal end of the body to a smaller diameter at the open distal end of the body, the tapered engagement surface configured to frictionally contact the fitting thread for retaining the protective cap in coupling engagement with the medical fluid fitting, wherein the tapered engagement surface is defined by one of a root of the cap thread or a crest of the cap thread,
wherein the protective cap peripherally surrounds the sealing portion without contacting the sealing surface when the protective cap is coupled with the medical fluid fitting.

13. The medical fluid fitting assembly of claim 12, wherein the tapered engagement surface is defined by a root of the cap thread and is configured to frictionally contact a crest of the fitting thread without contacting a root of the fitting thread when the protective cap is coupled with the medical fluid fitting.

14. The medical fluid fitting assembly of claim 12, wherein the tapered engagement surface is defined by the crest of the cap thread and is configured to frictionally contact a root of the fitting thread without contacting a crest of the fitting thread when the protective cap is coupled with the medical fluid fitting.

15. The medical fluid fitting assembly of claim 12, wherein the tapered engagement surface is formed with a non-included taper angle relative to a longitudinal axis of the body of the protective cap, the non-included taper angle ranging from approximately 1.5 degrees to approximately 3 degrees.

16. A method of protecting a sealing surface of a sealing portion of a medical fluid fitting using a protective cap, the sealing surface configured to form a fluid tight seal with a mating part so that fluid may pass through the medical fluid fitting, the method comprising:
positioning a cap thread provided on a body of the protective cap in coaxial alignment with a fitting thread provided on the medical fluid fitting;
threadedly engaging the cap thread with the fitting thread to releasably couple the protective cap with the medical fluid fitting;
frictionally contacting the fitting thread with a tapered engagement surface defined by the cap thread to retain the protective cap in coupling engagement with the medical fluid fitting, the tapered engagement surface tapering axially from a larger diameter at a proximal end of the body to a smaller diameter at an open distal end of the body; and
peripherally surrounding the sealing portion of the medical fluid fitting with the protective cap such that no portion of the protective cap contacts the sealing surface.

17. The method of claim 16, wherein the tapered engagement surface is formed with a non-included taper angle relative to a longitudinal axis of the body of the protective cap, the non-included taper angle ranging from approximately 1.5 degrees to approximately 3 degrees.

18. The method of claim 16, wherein frictionally contacting the fitting thread with the cap thread includes frictionally contacting a crest of the fitting thread with a tapered engagement surface defined by a root of the cap thread, the tapered engagement surface tapering axially relative to a longitudinal axis of the body of the protective cap.

19. The method of claim 16, wherein frictionally contacting the fitting thread with the cap thread includes frictionally contacting a root of the fitting thread with a tapered engagement surface defined by a crest of the cap thread, the tapered engagement surface tapering axially relative to a longitudinal axis of the body of the protective cap.

20. The method of claim 16, wherein the medical fluid fitting includes a male fitting and the sealing portion includes an axial protrusion defining the sealing surface, and peripherally surrounding the sealing portion includes receiving the axial protrusion within a bore of the body of the protective cap without contacting the sealing surface.

21. The method of claim 16, wherein the medical fluid fitting includes a female fitting and the sealing portion includes a socket and a circumferentially extending wall defining the sealing surface, and peripherally surrounding the sealing portion includes peripherally surrounding the circumferentially extending wall without contacting the sealing surface.

* * * * *